US012788283B2

(12) United States Patent
Yang

(10) Patent No.: US 12,788,283 B2
(45) Date of Patent: Nov. 10, 2026

(54) INSTALLATION UNIT OF ANALYTE DETECTION DEVICE AND USE METHOD

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 356 days.

(21) Appl. No.: 18/694,423

(22) PCT Filed: Sep. 27, 2021

(86) PCT No.: PCT/CN2021/120854
§ 371 (c)(1),
(2) Date: Mar. 22, 2024

(87) PCT Pub. No.: WO2023/044887
PCT Pub. Date: Mar. 30, 2023

(65) Prior Publication Data
US 2024/0382116 A1 Nov. 21, 2024

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/6848* (2013.01);
(Continued)

(58) Field of Classification Search
CPC ............. A61B 5/145–1495; A61M 2005/1585
See application file for complete search history.

(56) References Cited

U.S. PATENT DOCUMENTS 7,097,631 B2 * 8/2006 Trautman ............. A61B 17/205 604/93.01
2004/0133164 A1 7/2004 Funderburk et al.
(Continued)

FOREIGN PATENT DOCUMENTS

CN 1976627 6/2007
CN 102307518 1/2012
(Continued)

OTHER PUBLICATIONS

"International Search Report (Form PCT/ISA/210) of PCT/CN2021/120854," mailed on Jun. 29, 2022, pp. 1-4.

*Primary Examiner* — Adam J Eiseman
(74) *Attorney, Agent, or Firm* — JCIPRNET

(57) ABSTRACT

An installation unit of the analyte detection device and use method are provided. The installation unit includes: a housing, including at least two first buckles; a parallel slider module, which is provided with the second buckles corresponding to the first buckles, and the first buckles separately coupled with the second buckles; an analyte detection device; an auxiliary-needle module; an triggering module. When the triggering module moves to the far end relative to the housing, it cancels the coupling of the first buckles and the second buckles to implement the installation action; and an elastic module. When using the installation unit, the user only needs to attach the near end of the installation unit to the skin surface and press the housing at the far end to complete the installation of the analyte detection device, which is simple in structure and convenient in use.

18 Claims, 12 Drawing Sheets

(52) U.S. Cl.
CPC . *A61B 2560/045* (2013.01); *A61B 2560/0462* (2013.01); *A61B 2560/06* (2013.01); *A61B 2560/063* (2013.01)

(56) References Cited

U.S. PATENT DOCUMENTS

| | | | | |
|---|---|---|---|---|
| 2009/0124979 | A1* | 5/2009 | Raymond | A61M 5/14244 604/195 |
| 2010/0217105 | A1* | 8/2010 | Yodfat | A61B 5/14532 606/108 |
| 2010/0228226 | A1* | 9/2010 | Nielsen | A61M 5/158 604/506 |
| 2016/0278672 | A1* | 9/2016 | Cho | A61B 5/1473 |
| 2017/0188910 | A1* | 7/2017 | Halac | A61B 5/14865 |
| 2017/0290546 | A1* | 10/2017 | Antonio | A61B 5/14865 |
| 2022/0022787 | A1* | 1/2022 | Shen | A61B 5/150267 |
| 2022/0225899 | A1* | 7/2022 | Peterson | A61B 5/14503 |
| 2023/0027522 | A1* | 1/2023 | Antonio | A61B 5/14503 |
| 2023/0364331 | A1* | 11/2023 | List | A61B 5/14503 |

FOREIGN PATENT DOCUMENTS

| | | |
|---|---|---|
| CN | 113274001 | 8/2021 |
| TW | 202106253 | 2/2021 |
| WO | 2020231405 | 11/2020 |

* cited by examiner

INSTALLATION UNIT OF ANALYTE DETECTION DEVICE AND USE METHOD

CROSS-REFERENCE TO RELATED APPLICATION

This application is a 371 of international application of PCT application serial no. PCT/CN2021/120854, filed on Sep. 27, 2021. The entirety of the above mentioned patent application is hereby incorporated by reference herein and made a part of this specification.

TECHNICAL FIELD

The invention mainly relates to the field of medical devices, in particular to an analyte detection system.

BACKGROUND

The pancreas in a normal human body can automatically monitor the blood glucose level and automatically secrete required amount of insulin/glucagon. In the body of a type 1 diabetes patient, the pancreas does not function properly and cannot produce enough insulin for the body. Therefore, type 1 diabetes is a metabolic disease caused by abnormal pancreatic function, and diabetes is a lifelong disease. At present, there is no cure for diabetes with medical technology. The onset and development of diabetes and its complications can only be controlled by stabilizing blood glucose.

Diabetics need to have their blood glucose measured before they inject insulin into the body. At present, most of the testing methods can continuously measure blood glucose level and transmit the data to a remote device in real time for the user to view. This method is called Continuous Glucose Monitoring (CGM).

However, the current installation unit of analyte detection device has complex structure, cumbersome installation process, high production cost and inconvenience for users.

Therefore, the existing technology is in urgent need of a simple structure and user-friendly installation unit of analyte detection device.

BRIEF SUMMARY OF THE INVENTION

The invention discloses an installation unit of analyte detection device and use method, before installation, the first buckle on the shell of the analyte detection device is coupled with the second buckle on the parallel slider module. The analyte detection device is located at the front end of the parallel slider module. The connection between the auxiliary-needle module and the parallel slider module is releasable. Elastic module provides the elastic force required for installation. The user presses the housing to make the triggering module move to the far end relative to the housing, then the coupling between the first buckle and the second buckle can be released and the installation action can be implemented. The analyte detection device is installed on the user's skin surface, and the sensor is inserted into the user's skin at the same time. The installation unit of analyte detection device is simple in structure, convenient in use and low in production cost.

The first aspect of the invention provides an installation unit of analyte detection device, which comprises a housing, which comprises at least two first buckles; The parallel slider module is provided with the second buckle corresponding to the first buckle, and the second buckle is coupled with the first buckle; The analyte detection device is arranged at the front end of the parallel slider module, and the analyte detection device comprises a shell, a transmitter, a sensor and an internal circuit arranged in the shell which is electrically coupled with the sensor; The auxiliary-needle module, which connects with parallel slider module releasably, used to pierce the sensor into the user's skin; The trigger the module, relative to the shell to move to the far end, release the coupling of the first buckle and the second buckle, to implement the installation action; And an elastic module for providing the elastic force required to perform the installation action.

According to one aspect of the invention, the first buckle can be bent towards the outside of the housing, and when bent, the first buckle is uncoupled from the second buckle.

According to one aspect of the invention, the triggering module comprises a fixed buckle corresponding to the first buckle, which is in contact with the first buckle and prevents the first buckle from bending to the outside of the housing.

According to one aspect of the invention, the fixed buckle cancels contact with the first buckle when the triggering module moves to the far end relative to the housing.

According to one aspect of the invention, the first buckle, the second buckle and the fixed buckle are located at the same horizontal plane.

According to one aspect of the invention, the contact between the fixed buckle and the first buckle is one of point-contact, line-contact or surface-contact.

According to one aspect of the invention, when the contact between the fixed buckle and the first buckle is a surface-contact, and the contact surface is at a fixed angle with the horizontal plane and converges at the near end.

According to one aspect of the invention, the coupling place between the first buckle and the second buckle is plane.

According to one aspect of the invention, the plane is at a fixed angle with the horizontal plane and converges at the near end.

According to one aspect of the invention, the first buckles are spaced on the housing at equal angles.

According to one aspect of the invention, the number of first buckles is two, distributed on the housing at 180° intervals.

According to one aspect of the invention, the elastic module pushes the parallel slider module and the auxiliary-needle module towards the near end when performing the installation action.

According to one aspect of the invention, after the auxiliary-needle module moves toward the near end to a predetermined position, the parallel slider module disconnects from the auxiliary-needle module and the elastic module pushes the auxiliary-needle module back to its initial position.

According to one aspect of the invention, the front end of the analyte detection device also comprises tape for securing the analyte detection device to the user's skin surface.

Correspondingly, the invention also discloses an use method of the installation unit of an analyte detection device, which provides an installation unit comprising a housing, a parallel slider module, an auxiliary-needle module, an analyte detection device, a triggering module and an elastic module. The housing comprises at least two first buckles; The parallel slider module is provided with the second buckle corresponding to the first buckle, the second buckle is coupled with the first buckle; The analyte detection device is arranged at the front end of the parallel slider module, and the analyte detection device comprises a shell, a transmitter, a sensor and an internal circuit arranged in the shell which electrically couples with the sensor; The auxiliary-needle module, which is used to pierce the sensor into the user's skin, connects with parallel slider module releasably; When the triggering module moves to the far end relative to the housing, the coupling between the first buckle and the second buckle is removed to implement the installation action; The elastic module provides the elastic force required for installation action; The near end of the analyte detection device installation unit is attached to the user's skin surface; The user presses the shell at the far end, triggers the module to move to the far end relative to the shell, releases the coupling between the first buckle and the second buckle; The elastic module pushes the parallel slider module and the auxiliary-needle module toward the near end to install the analyte detection device on the user's skin surface, while the sensor is inserted into the user's skin; The parallel slider module is disconnected from the auxiliary-needle module, and the elastic module pushes the auxiliary-needle module back to its initial position; Remove the remaining parts of the analyte detection device installation unit.

According to one aspect of the invention, the first buckle can be bent towards the outside of the housing, and when bent, the first buckle is uncoupled from the second buckle.

According to one aspect of the invention, the triggering module comprises a fixed buckle corresponding to the first buckle. The fixed buckle is in contact with the first buckle to prevent the first buckle from bending to the outside of the housing.

According to one aspect of the invention, the fixed buckle cancels contact with the first buckle when the triggering module moves to the far end relative to the housing.

According to one aspect of the invention, the first buckle, the second buckle and the fixed buckle are at the same horizontal plane.

According to one aspect of the invention, the contact between the fixed buckle and the first buckle is one of point-contact, line-contact or surface-contact.

According to one aspect of the invention, the contact between the fixed buckle and the first buckle is a surface-contact, and the contact surface is a fixed angle with the horizontal plane and converges at the near end.

According to one aspect of the invention, the coupling place between the first buckle and the second buckle is plane.

According to one aspect of the invention, the plane is at a fixed angle with the horizontal plane and converges at the near end.

According to one aspect of the invention, the first buckles are spaced on the housing at equal angles.

According to one aspect of the invention, the number of first buckles is two, distributed on the housing at 180° intervals.

According to one aspect of the invention, the front end of the analyte detection device also comprises tape for securing the analyte detection device to the user's skin surface.

Compared with the prior art, the technical scheme of the invention has the following advantages:

The invention discloses an installation unit of analyte detection device, the first buckle on the housing is coupled with the second buckle on parallel slider module, the analyte detection device is arranged at the front end of the parallel slider module, auxiliary-needle module connects with the parallel slider module releasably, when the triggering module moves to the far end relative to the housing, the coupling between the first buckle and the second buckle can be released, so as to implement the installation action, the elastic module provides the elastic force required for the installation action. During the entire installation process, the user only needs to place the installation unit on the skin surface and press the housing toward the near end to install the analyte detection device on the skin surface while the sensor is pierced under the skin. The installation unit of analyte detection device is simple in structure, convenient in use and low in production cost.

Further, the coupling surface of the first buckle and the second buckle is a plane, and is at a fixed angle with the horizontal plane, converges at the near end, the elastic force by the elastic module acts on the near end of the parallel slider module, through the coupling surface of the second buckle and the first buckle, and produces a component towards the outside of the housing, so that the first buckle can be bent towards the outside of the housing to cancel the coupling between the first buckle and the second buckle, and the structure is simple.

Further, the fixed buckle on the triggering module is in contact with the first buckle, which can prevent the first buckle from bending to the outside of the housing, and thus also can prevent the parallel slider module moving to the near end. When the triggering module moves towards far end relative to the housing, the fixed buckle cancels connection with the first buckle, and the first buckle bends to the outside of the housing to decouple from the second buckle, the parallel slider module and the auxiliary-needle module move to the near end under the elastic force of the elastic module to implement the installation action, and the structure is simple.

Further, the first buckles are distributed on the housing at the same angle at intervals, accordingly, the second buckles are distributed on the parallel slider module at the same angle at intervals, and the fixed buckles are distributed on the triggering module at the same angle at intervals. In the process of use, the force of each module is uniform and the movement direction is consistent, which improves the reliability of the installation unit.

Further, after the auxiliary-needle module moves towards near end to a predetermined position, the connection between the auxiliary-needle and the parallel slider module is released, and the elastic module pushes the auxiliary-needle module back to the initial position, which is convenient to use.

According to the use method of the installation unit of the analyte detection device disclosed in the present invention, after the installation unit is attached to the user's skin surface, the user presses the housing at the far end, the triggering module moves to the far end relative to the housing to release the coupling between the first buckle and the second buckle, and then the elastic module pushes the parallel slider module and auxiliary-needle module moving towards the near end, the analyte detection device is installed on the user's skin surface, at the same time, the sensor is pierced under the skin. Then the parallel slider module is disconnected from the auxiliary-needle module, and the elastic module pushes the auxiliary-needle module back to the initial position. It is simple to use and enhances the user experience.

DETAILED DESCRIPTION

As mentioned above, the installation unit of analyte detection device with existing technology has complex structure, high production cost, inconvenient use and poor user experience.

In order to solve the problem, the present invention provides an installation unit of the analyte detection device, when in use, users attach the installation unit to the skin surface, press the housing at the far end, release the coupling state of the buckle, then the analyte detection device can be installed on the user's skin surface, and the sensor can be inserted under the skin.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the present invention.

In addition, it should be understood that the dimensions of the various components shown in the attached drawings are not necessarily drawn to actual proportions for ease of description, e.g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this manual.

It should be noted that similar labels and letters indicate similar items in the appending drawings below, so that once an item is defined or described in one of the appending drawings, there is no need to discuss it further in the subsequent appending drawings.

Figure 1:
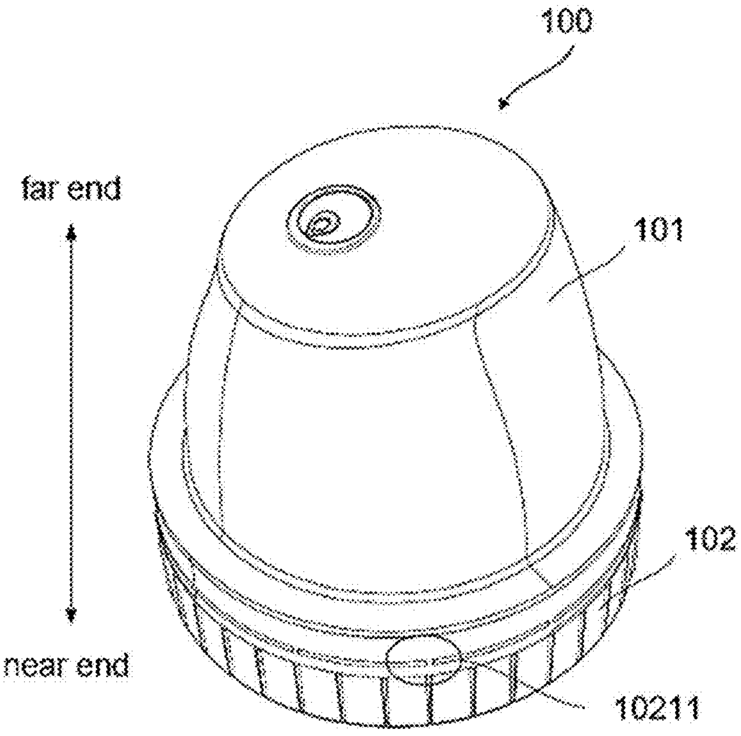
FIG. 1 is a schematic diagram of the external structure of the installation unit of the analyte detection device according to an embodiment of the invention.

FIG. 1 is a schematic diagram of the external structure of the installation unit of the analyte detection device in an embodiment of the present invention. The external structure of the installation unit 100 comprises a housing 101 for bearing the internal structural elements and a protective cover 102. The end of the installation unit 100 near the user's skin is the near end, and the end away from the skin is the far end. A first opening is arranged in the near end of housing 101. The protective cover 102 is used to protect, seal and prevent triggering of the internal structure and internal structural parts of the housing 101.

External Structure of the Housing

Figure 2A:
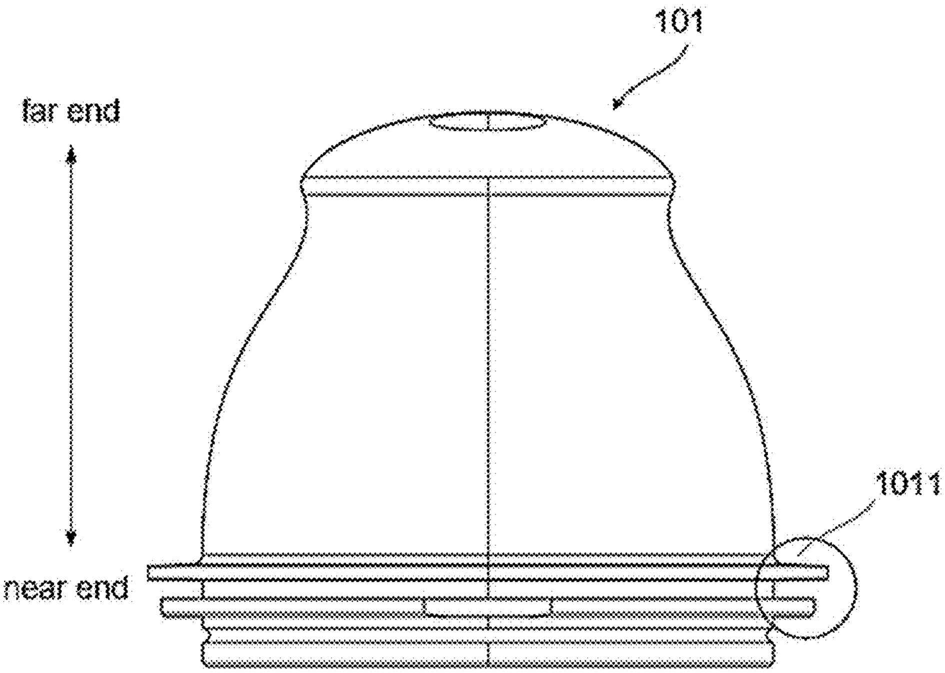
FIG. 2*a* is a schematic diagram of external structure of the housing according to an embodiment of the invention.
Figure 2B:
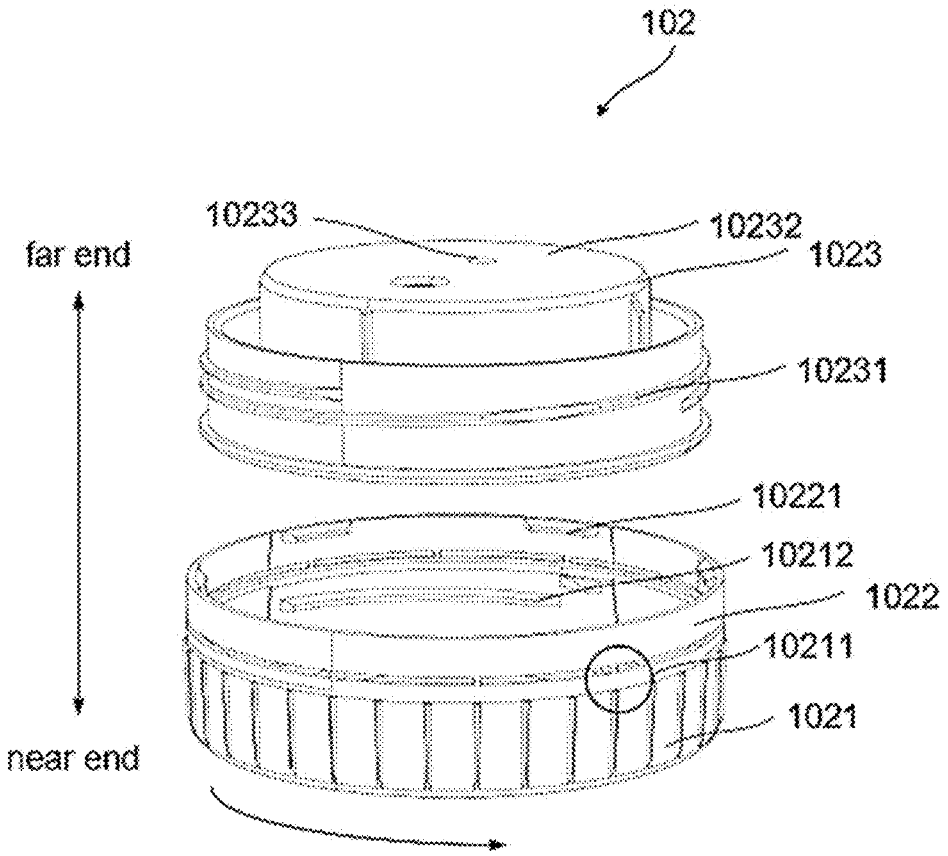
FIG. 2*b* is a schematic diagram of a protective cover according to an embodiment of the invention.

FIG. 2*a* is a schematic diagram of the external structure of the housing in an embodiment of the invention, and FIG. 2*b* is a schematic diagram of the protective cover. Protective cover 102 comprises outer cover 1021, clamp 1022 and inner cover 1023. The outer cover 1021 is provided with a second opening in the far end which faces the first opening. At the second opening, the outer cover 1021 is connected to the clamp 1022 by a breakable column 10211, which is distributed between the outer cover 1021 and the clamp 1022 at regular intervals. Column 10211 can be broken when the outer cover 1021 rotates relative to the clamp 1022, and the outer cover 1021 is separated from the clamp 1022.

The inner side of the outer cover 1021 is provided with an internal thread 10212, and the outer side of the inner cover 1023 is provided with an external thread 10231. The internal thread 10212 and the external thread 10231 can be connected to connect the outer cover 1021 and the inner cover 1023 together and keep fixed.

The inner side of the clamp 1022 is provided with a bulge 10221. Correspondingly, the outer side of the housing 101 is provided with a groove 1011, which forms a circle around the outer side of the housing and the bulge 10221 can be embedded into the groove 1011. The outer cover 1021 is fixed with the inner cover 1023 by screw thread, and then connected with the housing 101 by clamp 1022. The outer cover 1021 and the inner cover 1023 can protect, seal and prevent triggering of the internal structure of the housing 101. The anti-triggering function will be further described in the following.

In other embodiments of the invention, the outer cover 1021 and the inner cover 1023 can also be fixed by friction matching or buckle matching.

In other embodiments of the invention, the connection between clamp 1022 and housing 101 can also be realized by friction, buckle or thread.

Internal Structure of the Housing

Figure 3:
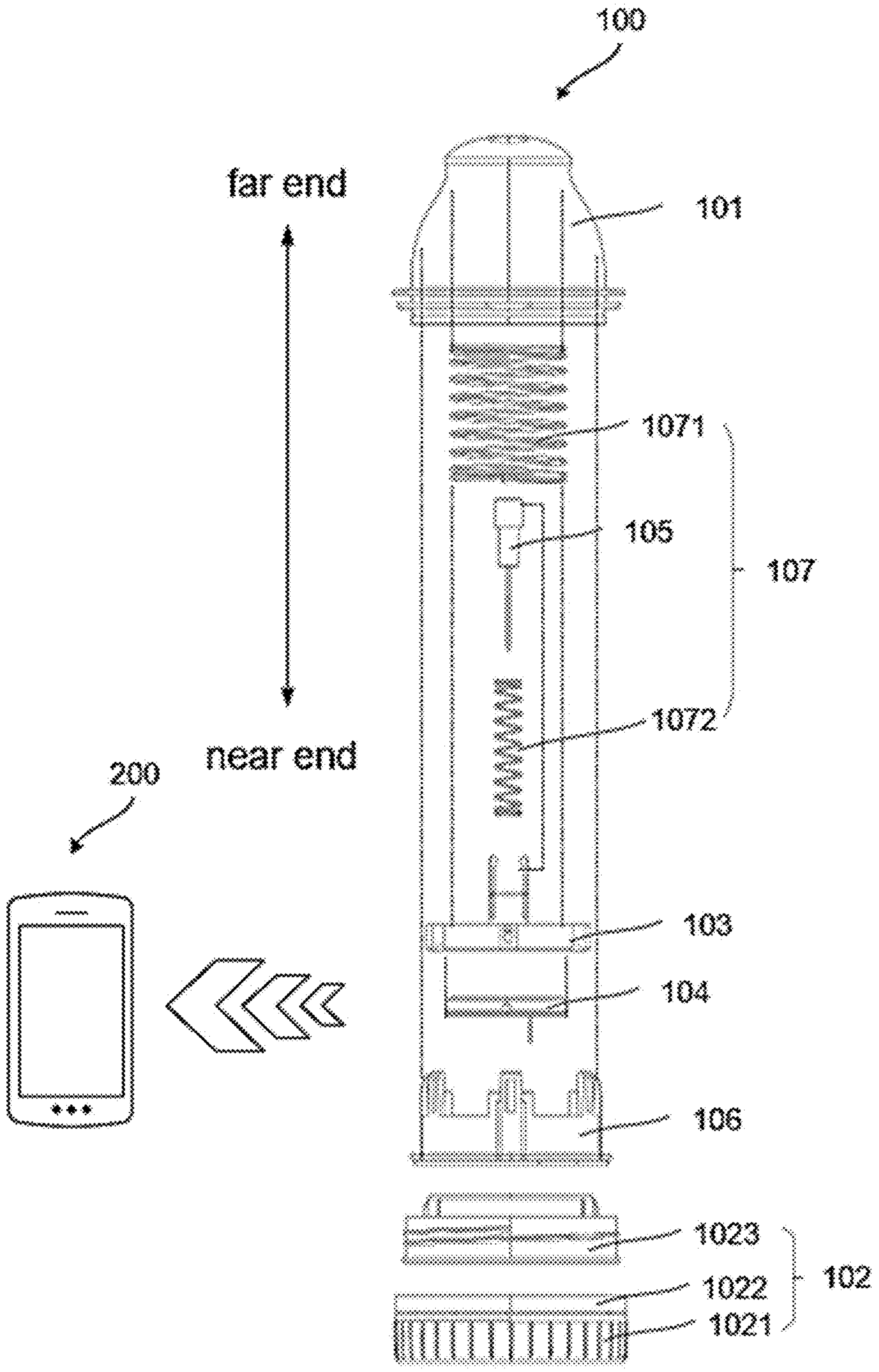
FIG. 3 is a schematic diagram of the explosive structure of the installation unit of the analyte detection device according to an embodiment of the invention.

FIG. 3 is the schematic diagram of explosive structure of the installation unit of analyte detection device in embodiment of the present invention, and the dotted line in the figure represents the installation and coordination relationship of each structural component. The internal structure of installation unit 100 of the analyte detection device comprises parallel slider module 103, analyte detection device 104, auxiliary-needle module 105, triggering module 106 and elastic module 107, which comprises the first elastic component 1071 and the second elastic component 1072.

Figure 4:
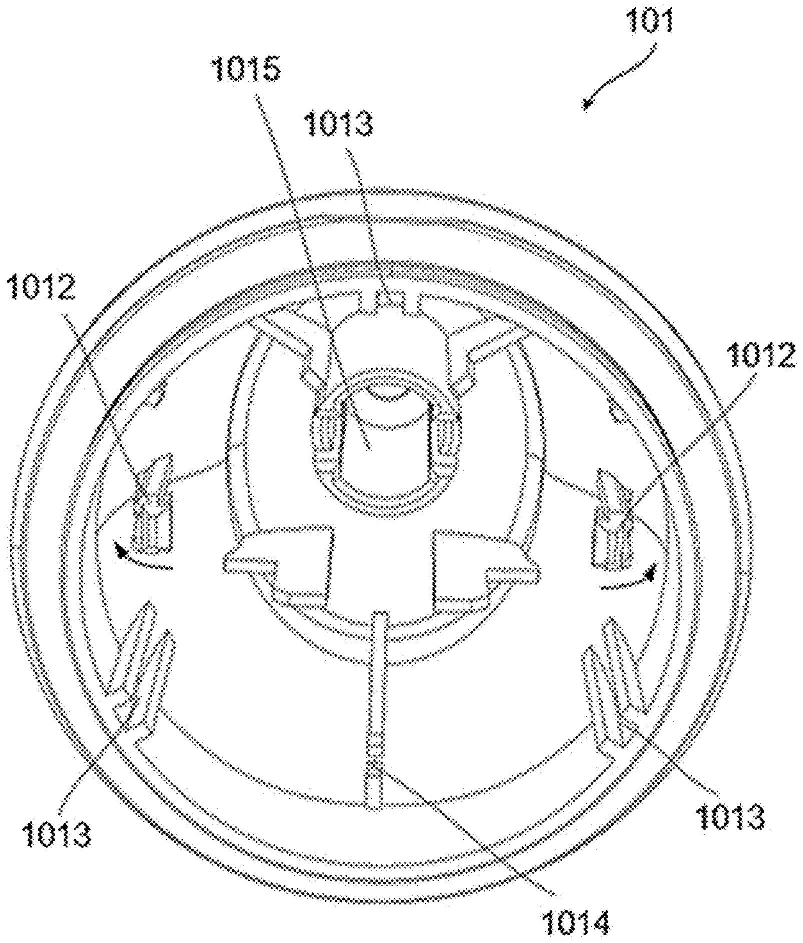
FIG. 4 is a schematic diagram of the internal structure of the housing according to an embodiment of the invention.

FIG. 4 is a schematic diagram of the internal structure of housing 101 in embodiment of the invention.

In an embodiment of the invention, at least two first buckles 1012 are arranged in the housing 101. The first buckle 1012 is integrated with the housing 101 and protrudes toward the near end of the housing 101. The first buckle 1012 is of flexible material and its end can be bent towards the outside of the housing 101.

In the preferred embodiment of the invention, the number of the first buckle 1012 is two, symmetrically distributed inside the housing 101, and the angle interval between each other is 180°.

In other preferred embodiments of the invention, the number of the first buckle 1012 is three or four, symmetrically distributed inside the housing 101, and the angle interval between them is 120° or 90°. The number of the first buckle 1012 can also be five or more, there is no limit here.

In the embodiment of the invention, housing 101 is also provided with at least two limit slots 1013, at least two slots 1014 and an auxiliary-needle limit slot 1015.

In an embodiment of the present invention, the limit slot 1013 comprises at least two rib plates projecting from the inner wall of housing 101. In preferred embodiments of the invention, the rib plates are parallel to each other and grooves are formed in the middle of adjacent rib plates.

In other embodiments of the invention, the limit slot 1013 is a slot that is sunken into the inner wall of housing 101.

Figure 10A:
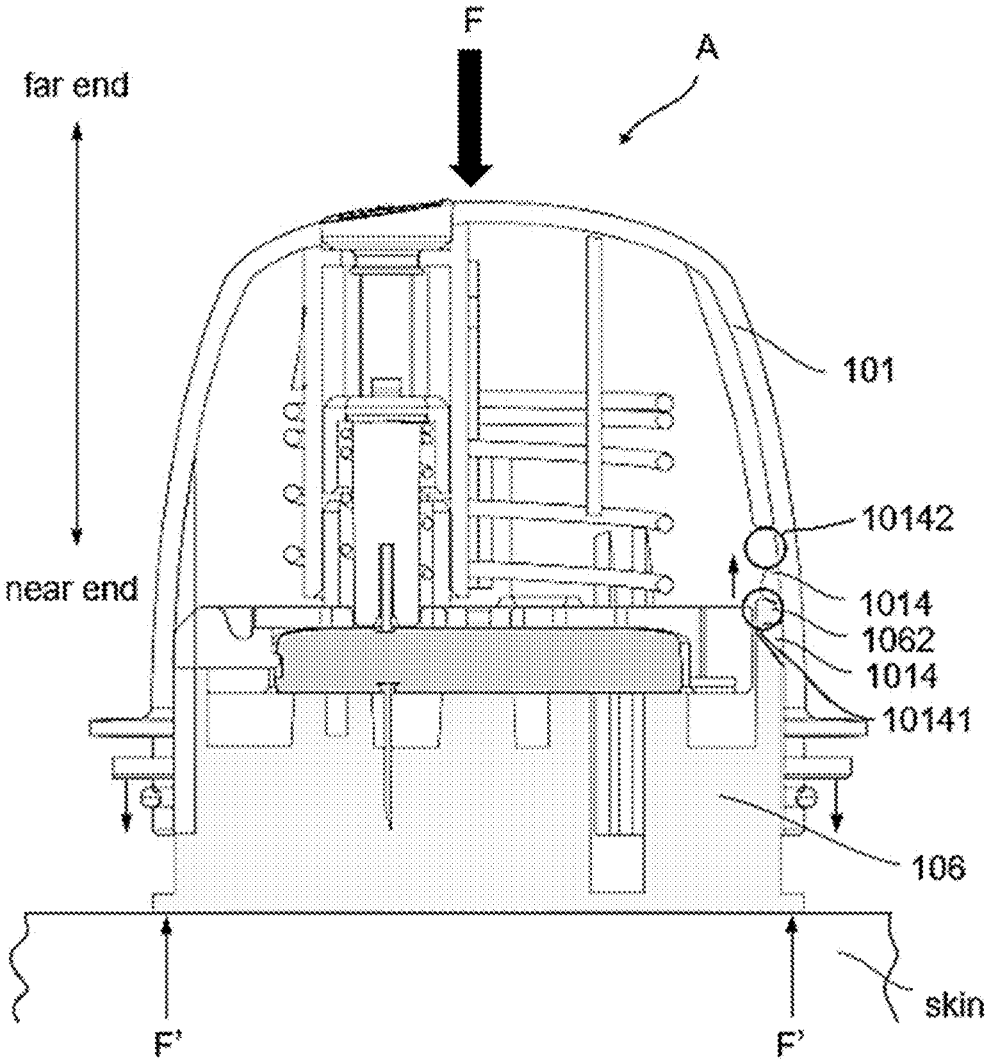
FIG. 10*a* is the schematic diagram of section A structure in FIG. 9.

In the embodiment of the present invention, slot 1014 comprises two card slots, namely, the first slot point 10141 and the second slot point 10142, as shown in FIG. 10*a*, the first slot point 10141 is closer to the near end relative to the second slot point 10142.

In the preferred embodiment of the invention, there are two limit slots 1013 and slots 1014, which are symmetrically distributed inside the housing 101 with an angle interval of 180° between them.

In other preferred embodiments of the invention, there are three or four limit slots 1013 and slots 1014, which are symmetrically distributed inside housing 101 with an angle interval of 120° or 90° between them. The number of limit slots 1013 and slots 1014 can also be five or more, there is no limit here.

Parallel Slider Module

Figure 5A:
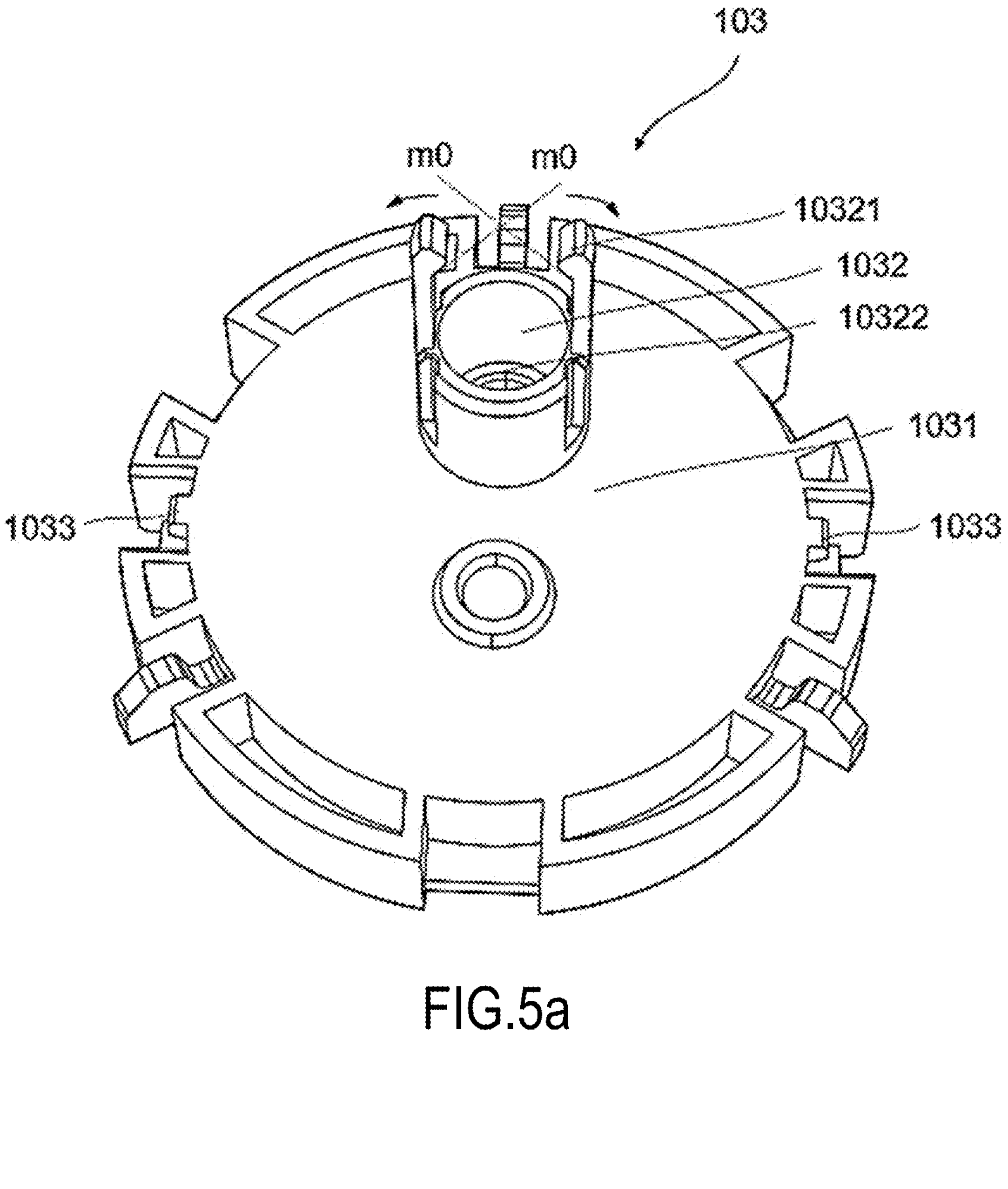
FIG. 5*a* is a structural schematic diagram of the far end of the parallel slider module according to an embodiment of the invention.
Figure 5B:
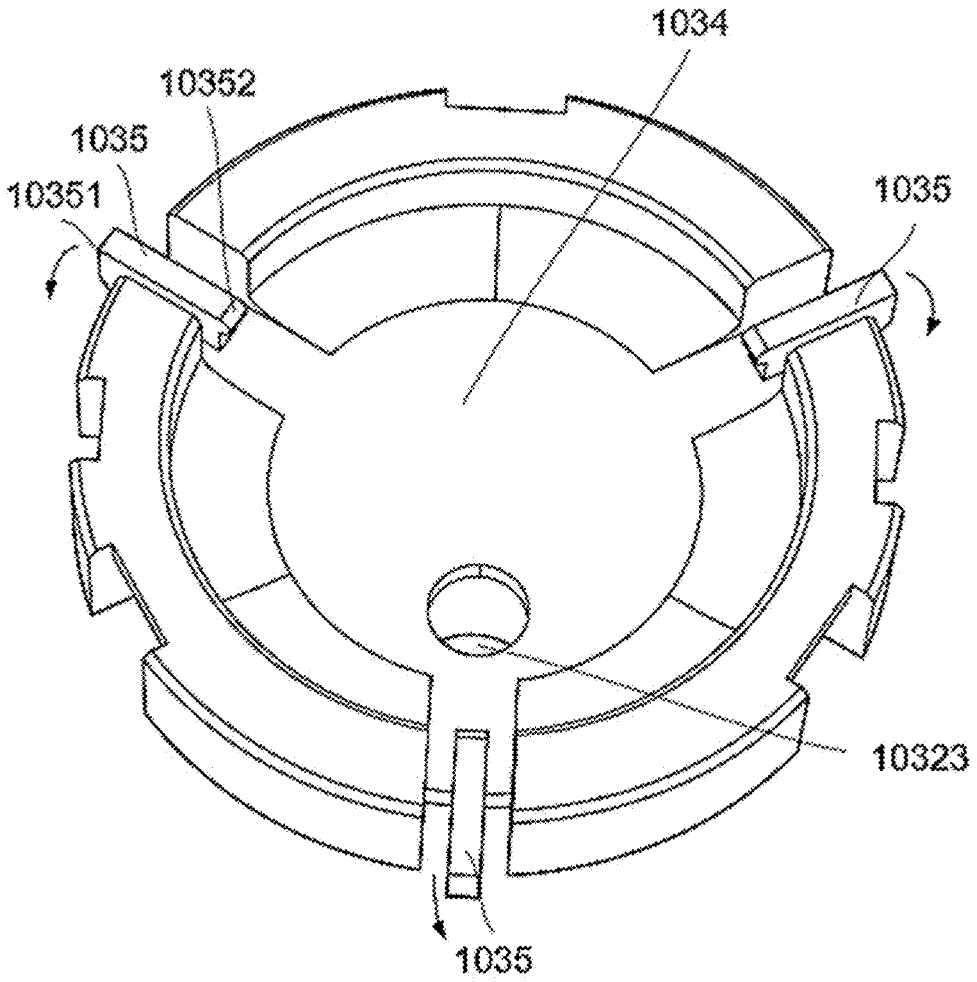
FIG. 5*b* is a structural schematic diagram of the near end of the parallel slider module according to an embodiment of the invention.

FIG. 5*a* is the structural diagram of the far end plane of parallel slider module 103, and FIG. 5*b* is the structural diagram of the near end plane of parallel slider module 103.

In the embodiment of the invention, the far end plane 1031 of the parallel slider module 103 is provided with a circular groove 1032 that protrudes to the far end. The circular groove 1032 is an internal hollowed cylindrical structure, and its inner diameter is d1. At least two slide-buckle 10321 are extended from the side wall of circular groove 1032 to the far end. The buckle part of the slide-buckle 10321 is plane or nearly plane, and is at a fixed angle with the horizontal plane, and its extended end m0 converges at the far end.

In an embodiment of the invention, the slide-buckle 10321 is a flexible material and can therefore be bent to the outside of the circular groove 1032.

In other embodiments of the invention, the slide-buckle 10321 may be directly arranged on the far end plane of the parallel slider module 103 without the need for a circular groove structure.

In the embodiment of the invention, the end of the circular groove 1032 near the far end plane 1031 is also provided with a boss 10322. The boss 10322 is an internally hollowed-out cylindrical structure with an inner diameter of d2, which can be understood as d1>d2. The circular groove 1032 and the boss 10322 of the internal hollowed-out structure form a through-hole 10323 that runs from the far end plane 1031 to the near end plane 1034 of the parallel slider module.

In the preferred embodiment of the invention, the number of slide-buckle 10321 is two, symmetrically distributed on the side wall of circular groove 1032, and the angle interval between the two slide-buckle 10321 is 180°.

In other preferred embodiments of the invention, the number of slide-buckles 10321 can be three or four, symmetrically distributed on the side wall of circular groove 1032, and the angle interval between slide-buckles 10321 is 120° or 90°. The number of slide-buckles 10321 can also be five or more, there is no limit here.

According to FIG. 5*a*, in an embodiment of the invention, at least two second buckles 1033 are arranged on the side of the far end plane 1031 of parallel slider module 103. The second buckles 1033 are symmetrically distributed on the side of 1031 on the far end plane with an Angle interval of 180° between them.

In other embodiments of the invention, the number of the second buckles 1033 is three or four, symmetrically distributed on the side of the far end plane 1031, and the angle interval between them is 120° or 90°. The number of the second buckles 1033 can also be five or more, there is no limit here. In installation unit 100, the second buckle 1033 is coupled to the first buckle 1012. The position and number of the second buckle 1033 is the same as the first buckle 1012.

According to FIG. 5*b*, in the embodiment of the present invention, at least two T-shaped structure 1035 are arranged on the side of the near end plane 1034 of parallel slider module 103. The vertical part of T-shaped structure 1035 is connected to the near end plane 1034, and the horizontal part comprises T-shaped-structure slider 10351 and T-shaped-structure buckle 10352. The T-shaped-structure slider 10351 is oriented to the outside of the parallel slider module 103 and protrudes out of the outer ring of the parallel slider module 103; T-shaped-structure buckle 10352 faces the inside of the parallel slider module 103 and protrudes from the inner ring of the parallel slider module 103.

In installation unit 100, T-shaped-structure slider 10351 is located in limit slot 1013 to limit the position of parallel slider module 103 and prevent rotation of parallel slider module 103. The number and position of T-shaped-structure slider 10351 are the same as that of limit slot 1013. In the process of moving the parallel slider module 103 towards the near end, the T-shaped-structure slider 10351 slides in the limit slot 1013.

In the preferred embodiment of the invention, the vertical part of T-shaped structure 1035 is a flexible material, the vertical part and the horizontal part are formed in one piece, and thus the horizontal part can be bent around the vertical part.

In other preferred embodiment of the invention, the vertical part of T-shaped structure 1035 is elastic material, such as spring, shrapnel, etc., and the horizontal part is fixedly connected with the vertical part through welding or hot melting processes, and the horizontal part can also be bent around the vertical part.

Analyte Detection Device

Figure 6:
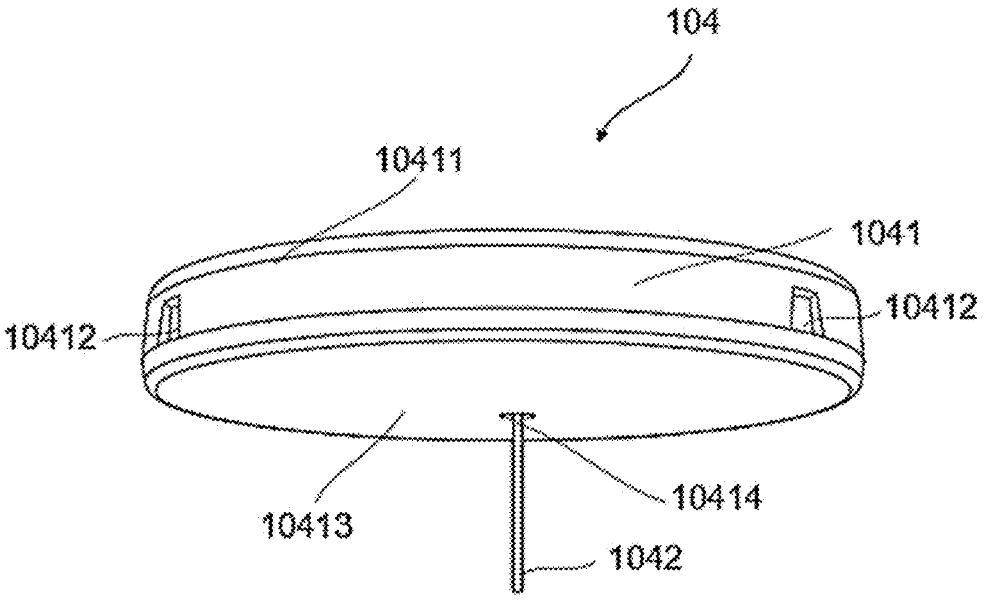
FIG. 6 is a schematic diagram of the analyte detection device according to an embodiment of the invention.

FIG. 6 is a schematic diagram of the analyte detection device in an embodiment of the present invention.

In combination with FIG. 3, in an embodiment of the present invention, the analyte detection device 104 comprises a shell 1041, a transmitter (not shown in the figure), a sensor 1042 and an internal circuit (not shown in the figure) arranged in the shell 1041 which electrically couples with the sensor. Sensor 1042 is used to detect the parameter information of user's body fluid analyte, and transmits the parameter information of the analyte to the transmitter through the internal circuit, and then from the transmitter to the external equipment 200.

In the preferred embodiment of the invention, before the analyte detection device 104 is installed on the user's skin surface, the signal is transmitted to the external device 200 at the first frequency $f_1$, and after it is installed on the user's skin surface, the signal is transmitted to the external device 200 at the second frequency $f_2$, and the second frequency $f_2$ is greater than the first frequency $f_1$. In further preferred embodiments of the invention, the first frequency $f_1$ is 0~12 times/hour and the second frequency $f_2$ is 12~3600 times/hour.

In the preferred embodiment of the invention, the first frequency $f_1$ is 0 times/hour, that is, before the analyte detection device 104 is installed on the user's skin surface, no signal is transmitted to the external device 200, so as to save the power consumption of the analyte detection device 104 before installation.

In an embodiment of the invention, the shell 1041 comprises an upper-outer-shell 10411 and a lower-outer-shell 10413, and the upper-outer-shell 10411 and the lower-outer-shell 10413 are spliced together to form an internal space. The sensor 1042 consists of an external part (not shown) and an internal part (not shown). The external part, the transmitter and the internal circuit are arranged in the internal space and the external part is electrically coupled to the internal circuit. The internal part is provided with electrodes, membranes and other structures, which can be inserted into the user's skin to detect the parameters of the analyte. When the internal part is inserted under the skin, it needs to be inserted at the correct angle, such as perpendicular to the skin surface. At the end of its life, the analyte detection device 104 is removed from the user's skin surface and discarded as a whole.

In the embodiment of the invention, the lower-outer-shell 10413 comprises the first through-hole 10414. Correspondingly, on the axis of the first through-hole 10414, the upper-outer-shell 10411 comprises the second through-hole (not shown in the figure), and the internal part passes through the first through-hole 10414 to the outside of the shell, so as to penetrate the user's subcutaneous skin.

In the embodiment of the invention, the side of the upper-outer-shell 10411 comprises buckle hole 10412 corresponding to T-shaped-structure buckle 10352, where "corresponding" means that the position and number of buckle hole 10412 are consistent with that of T-shaped-structure buckle 10352. In the installation unit 100, the upper-outer-shell 10411 is fitted with the near end face 1034, the T-shaped-structure buckle 10352 forms a buckle-connection with the buckle hole 10412, and the analyte detection device 104 is fixed on the parallel slider module 103. When the horizontal part of the T-shaped structure 1035 is bent around the vertical part, the buckle-connection between the T-shaped-structure buckle 10352 and the buckle hole 10412 is removed, and the analyte detection device 104 is separated from the parallel slider module 103. Therefore, in installation unit 100, analyte detection device 104 and parallel slider module 103 are releasable connection.

Auxiliary-Needle Module

Figure 7:
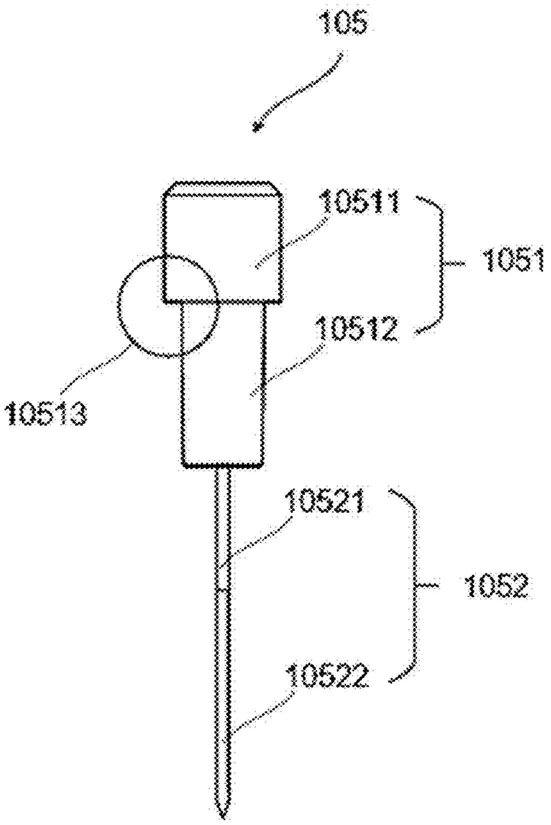
FIG. 7 is a schematic diagram of the auxiliary-needle module according to an embodiment of the invention.

FIG. 7 is a schematic diagram of the auxiliary-needle module in an embodiment of the invention.

In an embodiment of the invention, the auxiliary-needle module 105 comprises an auxiliary-needle fixed structure 1051 and an auxiliary-needle 1052. In the installation unit 100, the auxiliary-needle fixed structure 1051 is located at the far end relative to the auxiliary-needle 1052.

In the embodiment of the invention, the auxiliary-needle fixed structure 1051 comprises an auxiliary-needle slide block 10511 and an auxiliary-needle fixed block 10512. The diameter or width of the auxiliary-needle slide block 10511 is larger than that of the auxiliary-needle fixed block 10512, forming a convex surface 10513 toward the near end.

In the embodiment of the invention, the auxiliary-needle 1052 comprises a fully-enclosed needle body 10521 and a semi-enclosed needle body 10522. The fully-enclosed needle body 10521 is located between the auxiliary-needle fixed block 10512 and the semi-enclosed needle body 10522, and is fixedly connected with the auxiliary-needle fixed block 10512. The hollow structure of the semi-enclosed needle 10522 can be used to accommodate the internal part of the sensor 1042. When the semi-enclosed needle 10522 is inserted into the user's skin, the internal part can be also inserted into the user's skin, and the state of the internal part is not affected when the needle is retracted.

In other embodiments of the invention, the auxiliary-needle 1052 only comprises the semi-enclosed needle body 10522, that is, the semi-enclosed needle body 10522 is fixedly connected with the auxiliary-needle fixed block 10512, which can reduce the material used for the auxiliary-needle 1052 and save costs, but also reduce the rigidity of the auxiliary-needle 1052.

In installation unit 100, auxiliary-needle 1052 passes through the second through-hole and the first through-hole 10414 successively, thus passing through analyte detection device 104. The internal part of sensor 1042 is located in semi-enclosed needle body 10522.

Triggering Module

Figure 8:
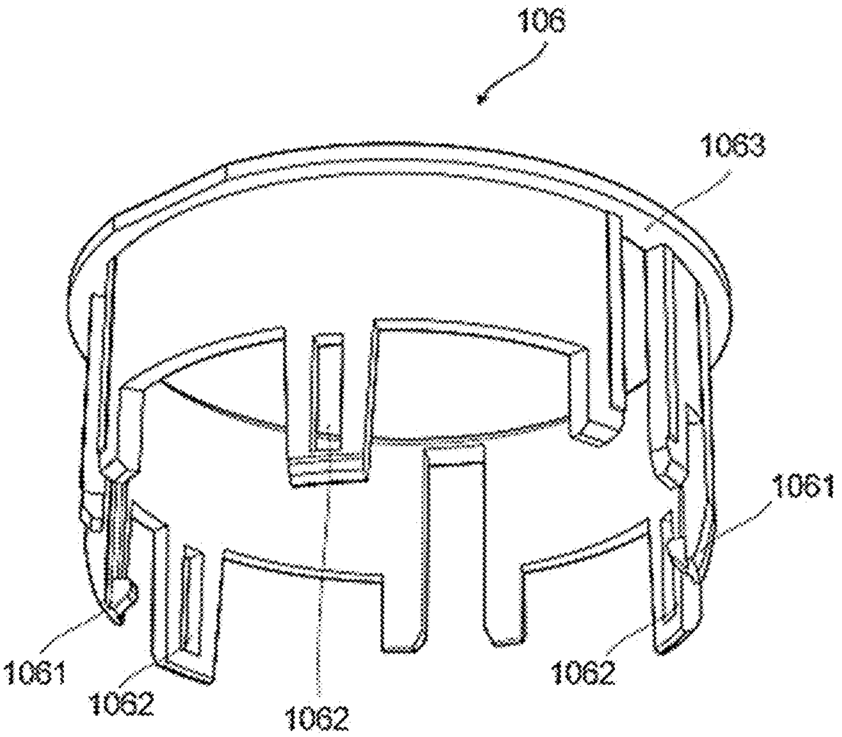
FIG. 8 is a schematic diagram of the triggering module according to an embodiment of the invention.

FIG. 8 is a schematic diagram of the triggering module in an embodiment of the invention.

In an embodiment of the invention, the triggering module 106 is provided with at least two fixed buckle 1061 corresponding to the first buckle 1012. In installation unit 100, the fixed buckle 1061 is in contact with the first buckle 1012 to prevent the first buckle 1012 from bending to the outside of the housing 101. The contact between the fixed buckle 1061 and the first buckle 1012 can be point-contact, line-contact or surface-contact. When the contact is surface-contact, the contact surface between the fixed buckle 1061 and the first buckle 1012 is at a fixed angle with the horizontal plane and converges at the near end of the installation unit 100. The number and position of the fixed buckle 1061 is the same as the first buckle 1012.

In the embodiment of the invention, there are also at least two lugs 1062 arranged on the triggering module 106. In the installation unit 100, the lug 1062 and the slot 1014 snap together to fix the triggering module 106. The number and position of lug 1062 are the same as slot 1014. According to FIG. **10*a*, before installation unit 100 is used, lug 1062 is located in slot 10141 of the first buckle. At this point, the fixed buckle 1061 is in contact with the first buckle 1012**.

In an embodiment of the invention, the triggering module 106 also comprises an outer ring 1063, which connects the fixed buckle 1061 and the lug 1062 into an integral whole. In installation unit 100, the outer ring 1063 is proximal to the first opening and protrudes from the first opening relative to the lug 1062. In using installation unit 100, the outer ring 1063 is attached to the user's skin surface.

Elastic Module

According to FIG. 3, the elastic module 107 comprises the first elastic component 1071 and the second elastic component 1072.

In the embodiment of the invention, the first elastic component 1071 is located between the parallel slider module 103 and the housing 101, that is, one end of the first elastic component 1071 is located on the far end plane of the parallel slider module 103, and the other end is located in the housing 101. In the installation unit 100, the first elastic component 1071 is in compression state and can provide elasticity.

In the embodiment of the invention, the second elastic component 1072 is located between parallel slider module 103 and auxiliary-needle module 105, that is, one end of the second elastic component 1072 is located on the boss 10322 of parallel slider module 103 and the other end is located on the convex surface 10513 of auxiliary-needle module 105. In the installation unit 100, the second elastic component 1072 is in a compressed state to provide elasticity.

In the preferred embodiment of the invention, the first elastic component 1071 or the second elastic component 1072 is a metal spring.

In the embodiment of the invention, the inner ring diameter of the first elastic component 1071 is larger than the outer ring diameter of the circular groove 1032 and the auxiliary-needle slide block 10511. In the installation unit 100, the first elastic component 1071 is surrounded by the outer side of the auxiliary-needle slide block 10511 and the circular groove 1032, so that the internal space of the installation unit 100 can be fully utilized.

In the embodiment of the invention, the outer ring diameter of the second elastic component 1072 is larger than the outer diameter of the auxiliary-needle fixed block 10512 and the inner diameter of the boss 10322, but smaller than the outer diameter of the auxiliary-needle slide block 10511 and the inner diameter of the circular groove 1032. Therefore, one end of the second elastic component 1072 is placed in the circular groove 1032. The other end is enclosed outside the auxiliary pin fixing block 10512 to make full use of the internal space of the installation unit 100.

Use Method of Installation Unit

Figure 9:
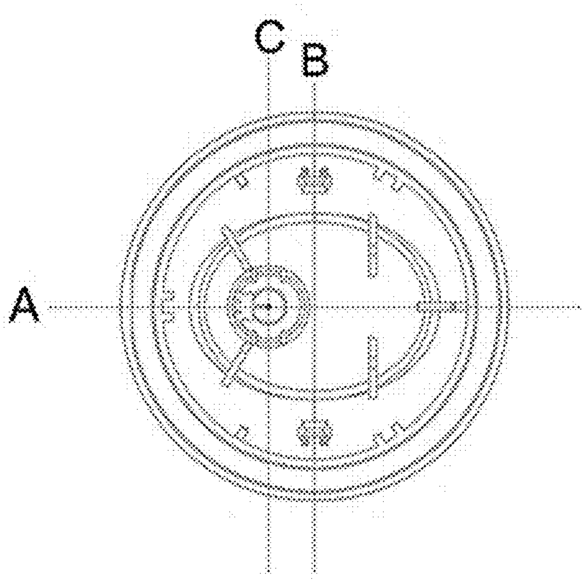
FIG. 9 is a top view of the installation unit according to an embodiment of the invention.

FIG. 9 is the top view of the installation unit of the embodiment of the invention.

FIG. 10*a* is the schematic diagram of section A structure in FIG. 9.

Figure 10B:
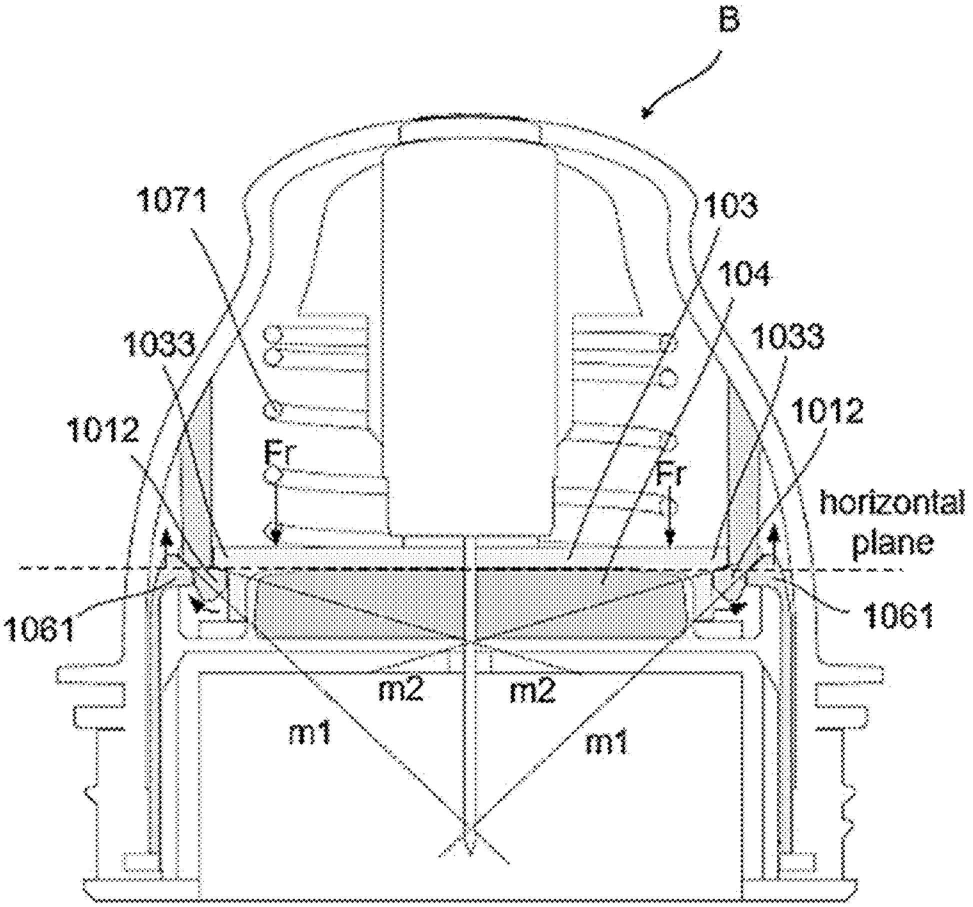
FIG. 10*b* is the schematic diagram of section B structure in FIG. 9.

FIG. 10*b* is the schematic diagram of section B structure in FIG. 9.

Figure 10C:
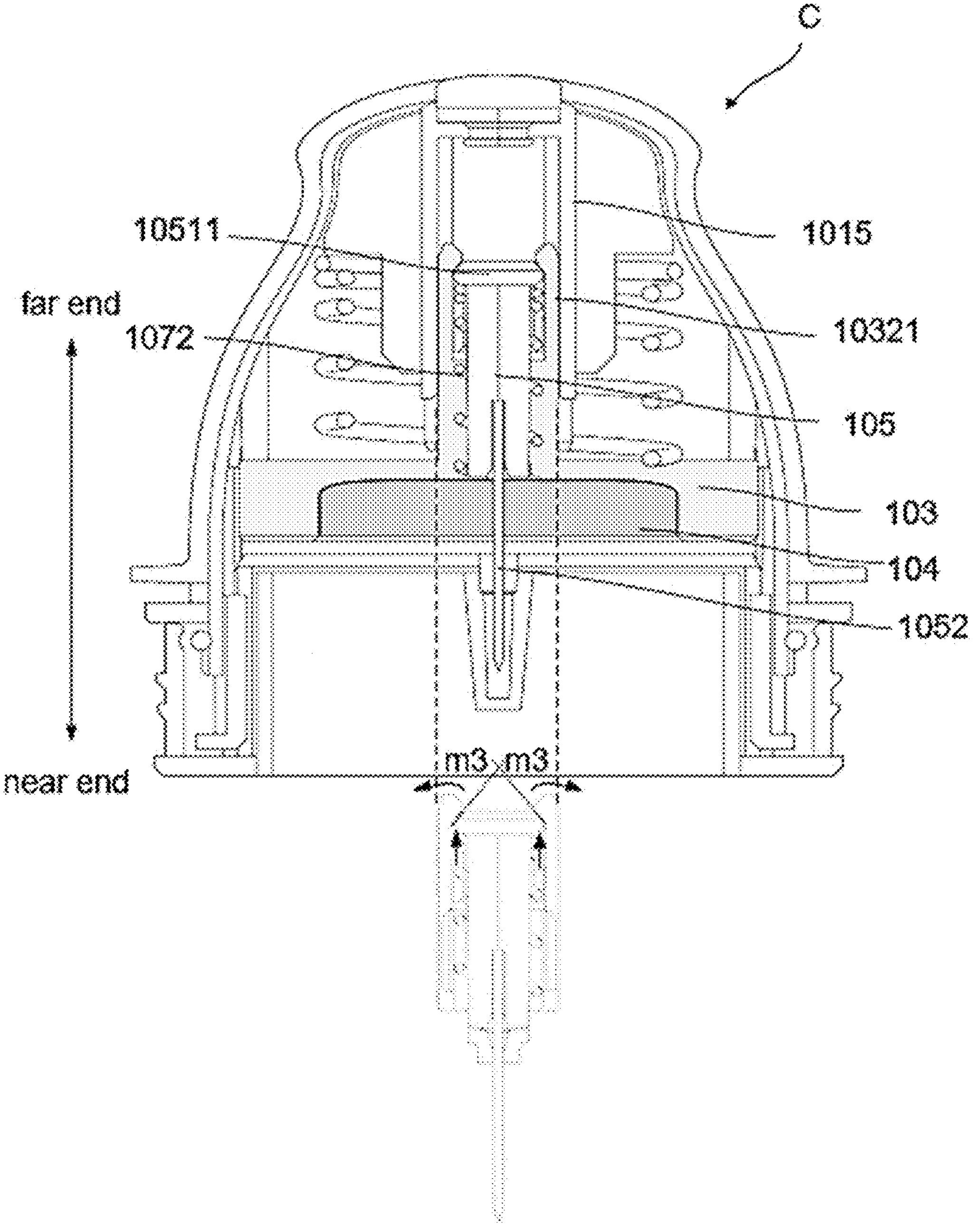
FIG. 10*c* is the schematic diagram of section C structure in FIG. 9.

FIG. 10*c* is the schematic diagram of section C structure in FIG. 9.

Figure 11:
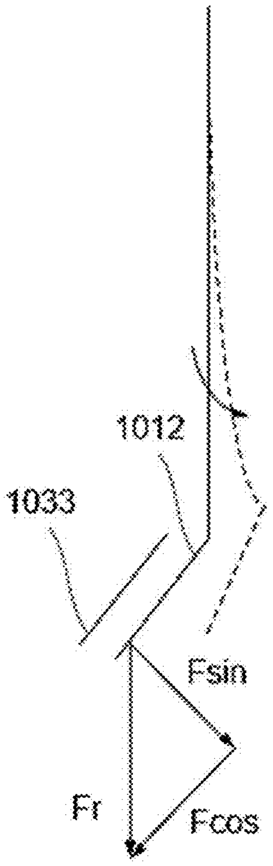
FIG. 11 is the bending schematic diagram of the first buckle because of force according to an embodiment of the invention.

FIG. 11 shows the bending diagram of the first buckle.

According to FIG. 10*a* and FIG. 10*b*, in the embodiment of the present invention, the slot 1014 is provided with the first slot point 10141 and the second slot point 10142. Before the installation unit 100 is used, triggering module 106 is fixed to the housing 101 through the coupling of lug 1062 and slot 10141, at this time, the fixed buckle 1061 is in contact with the first buckle 1012 to prevent the first buckle 1012 from bending to the outside of the housing 101. The fixed buckle 1061, the first buckle 1012 and the second buckle 1033 are at the same horizontal plane. In the preferred embodiment of the invention, the second buckle 1033, the first buckle 1012 and the fixed buckle 1061 are successively arranged from the housing 101 inside out.

In the embodiment of the invention, the contact between the fixed buckle 1061 and the first buckle 1012 is one of point-contact, line-contact or surface-contact. When the above contact is surface-contact, the extension line m1 of the contact surface converging at the near end. This kind of structural design can make the fixed buckle 1061 move toward the far end relative to the first buckle 1012.

In the preferred embodiment of the invention, the coupling surface of the second buckle 1033 and the first buckle 1012 is a plane, which has a fixed angle with the horizontal plane, and its extended line m2 converges at the near end.

With reference to FIG. 11, this kind of structural design can make the second buckle 1033 move toward the near end relative to the first buckle 1012, and push the first buckle 1012 toward the outside of the housing 101, so as to release the coupling state between the first buckle 1012 and the second buckle 1033.

In an embodiment of the invention, the first elastic component 1071 is in a state of compression and has elastic potential energy, and its self-elasticity gives thrust Fr to the near end of parallel slider module 103. The thrust Fr acts on the first buckle 1012 through the coupling surface of the second buckle 1033 and the first buckle 1012. And generate a component force Fsin perpendicular to the plane of the first buckle 1012, which can push the first buckle 1012 toward the outside of the housing 101 to bend, so as to release the coupling state of the first buckle 1012 and the second buckle 1033.

In the embodiment of the invention, when the installation unit 100 is used, the outer cover 1021 is rotated to break the column 10211, the protective cover 102 is separated from the housing 101, and the near end of the installation unit 100 is close to the user's skin until the outer ring 1063 of triggering module 106 is triggered to stick to the skin surface, and the user presses the housing 101 at the far end. The housing 101 moves toward the skin, while the triggering module 106 remains stationary. Therefore, the triggering module 106 moves toward the far end relative to the housing 101, and the lug 1062 disconnects from the first slot point 10141 and enters the second slot point 10142. Meanwhile, the fixed buckle 1061 no longer contacts with the first buckle 1012. The coupling state between the first buckle 1012 and the second buckle 1033 is released due to the bending of the component force Fsin toward the outside of the housing 101.

In the embodiment of the invention, after the coupling state is released, the parallel slider module 103 continues to move toward the near end under the elastic force of the first elastic component 1071, and drives the analyte detection device 104 to move toward the near end until the lower-outer-shell 10413 of the analyte detection device 104 contacts the user's skin surface.

According to FIG. 10*c*, in the embodiment of the invention, the slide-buckles 10321 is connected with the auxiliary-needle slide block 10511. When the first elastic component 1071 pushes the parallel slider module 103 to move toward the near end, the auxiliary-needle module 105 is driven to move toward the near end together.

In an embodiment of the invention, the connection point of slide-buckles 10321 and auxiliary-needle slide block 10511 is a plane or approximate plane, which has a fixed angle with the horizontal plane, and the extension line m3 converges at the far end. The thrust force of the second elastic component 1072 on the auxiliary-needle slide block 10511 is toward the far end, so the auxiliary-needle slide block 10511 can push the slide-buckles 10321 toward the outside of the housing 101, making the slide-buckles 10321 bend, the principle of which is equivalent to FIG. 11.

In the embodiment of the invention, in the installation unit 100, the side wall of the limit slot 1015 of the auxiliary needle prevents the slide-buckles 10321 from bending, and the connection state of the slide-buckles 10321 and the auxiliary-needle slide block 10511 clasp does not change. As parallel slider module 103 and auxiliary-needle module 105 move towards the near end, the slide-buckles 10321 is separated from the auxiliary-needle limit slot 1015, and the inner wall of the auxiliary-needle limit slot 1015 no longer prevents the slide-buckles 10321 from bending. The second elastic component 1072 pushes the auxiliary-needle slide block 10511 to the far end. At the same time, the auxiliary-needle slide block 10511 pushes the slide-buckle 10321 to bend outwards, and the connection between the slide-buckle 10321 and the auxiliary-needle slide block 10511 is released. The second elastic component 1072 continues to push the auxiliary-needle slide block 10511 to move toward the far end, and finally the auxiliary-needle module 105 returns to its initial position. Auxiliary-needle 1052 retracted into housing 101 to prevent auxiliary-needle 1052 from being exposed to housing 101 and causing unnecessary damage.

In the embodiment of the invention, when the slide-buckles 10321 is detached from the limit slot 1015 of the auxiliary-needle, the semi-enclosed needle body 10522 of the auxiliary-needle penetrates the user's subcutaneous.

In the embodiment of the invention, in the installation unit 100, the T-shaped-structure slider 10351 is located in the limit slot 1013, and the limit slot 1013 restricts the position and direction of the parallel slider module 103 through the T-shaped-structure slider 10351 to ensure that the parallel slider module 103 is perpendicular to its sliding direction. Thus, the analyte detection device 104 set at the front end of the parallel slider module 103 is kept perpendicular to its motion direction, and the auxiliary-needle 1052 is kept parallel to its motion direction, so that the part of the sensor inside the auxiliary-needle 1052 and its envelope can pierce the user's skin at a vertical angle to relieve the user's pain.

In the embodiment of the invention, in the process of parallel slider module 103 sliding towards the near end, the T-shaped-structure slider 10351 slides in the limit slot 1013 until it touches the outer ring 1063 of the triggering module 106. Driven by the first elastic component 1071, the parallel slider module 103 continues to move towards the near end. The outer ring 1063 stops the T-shaped-structure slider 10351 from moving toward the near end, so the T-shaped-structure slider 10351 is bent around the vertical part, the T-shaped-structure buckle 10352 is disconnected from the buckle hole 10412, and the analyte detection device 104 is separated from the parallel slider module 103, so that it can be installed on the user's skin surface.

In the embodiment of the invention, when the T-shaped-structure slider 10351 contacts with the outer ring 1063, the position of the parallel slider module 103 is a predetermined position. At this time, the lower-outer-shell 10413 of the analyte detection device contacts the user's skin surface.

In an embodiment of the invention, the auxiliary-needle 1052 passes through the second through-hole and the first through-hole 10414 in turn, and through the analyte detection device 104. Meanwhile, the semi-enclosed needle body 10522 of the auxiliary-needle 1052 envelope sensor 1042. In the process of parallel slider module 103 and auxiliary-needle module 105 moving towards the near end, the semi-enclosed needle body 10522 with sensor 1042 penetrated into the subcutaneous body. After the auxiliary-needle 1052 retracted, the internal part of sensor 1042 remained under the subcutaneous body, and the state of the internal part of sensor 1042 was not affected when the auxiliary-needle 1052 retracted.

In the embodiment of the invention, the user is required to press the housing 101 at the far end and apply force F to the housing 101 at the near end to trigger the outer ring 1063 of triggering module 106 to contact the user's skin surface, and the user's skin provides force F' of outer ring 1063 that is opposite to force F, so as to realize the relative movement of triggering module 106 and housing 101. During the actual installation, the absolute position of the triggering module 106 remains unchanged, and the housing 101 moves toward the near end.

Before the installation, in order to prevent the triggering module 106 from moving relative to the housing 101, a protective cover 102 is installed at the near end of the housing 101. The protective cover 102 is surrounded by the outer ring 1063 of the triggering module 106, so as to prevent the installation action from being carried out in an incorrect position due to the accidental collision of the outer ring 1063.

At the same time, the auxiliary-needle 1052 and the sensor 1042 are extended into the groove of the inner cover 10233, which can play a sealing role and prevent the outside dust, particles and other dirt from contacting the needle body and the sensor and causing pollution.

In embodiments of the invention, adhesive tape is also arranged on the lower-outer-shell 10413 (not shown in the figure) of the analyte detection device to fix the analyte detection device 104 on the user's skin surface.

To sum up, the present invention discloses an installation unit of the analyte detection device and use method, the first buckle of the housing is coupled with the second buckle of the parallel slider module, the coupling between the first buckle and the second buckle can be released when the triggering module moves to the far end relative to the housing, and then implement installation action, when using the installation unit, users only need to attach the near end of the installation unit to the skin surface and press the housing at the far end to realize the installation of the analyte detection device. The installation unit is simple in structure and convenient in use, enhancing the user experience.

Although some specific embodiments of the invention have been detailed through examples, technicians in the field should understand that the above examples are for illustrative purposes only and are not intended to limit the scope of the invention. Persons skilled in the field should understand that the above embodiments may be modified without departing from the scope and spirit of the present invention. The scope of the invention is limited by the attached claims.

The invention claimed is:

1. An installation unit of an analyte detection device, comprising:

a housing, comprising at least two first buckles;

a parallel slider module, provided with second buckles corresponding to the at least two first buckles, and the at least two first buckles and the second buckles are releasably coupled at a coupling in an initial pre-installation configuration;

an analyte detection device arranged at a front end of the parallel slider module, wherein the analyte detection device comprises a shell, a transmitter, a sensor and an internal circuit arranged in the shell and electrically coupled with the sensor;

an auxiliary-needle module, wherein the auxiliary-needle module and the parallel slider module are releasably connected to each other, and the auxiliary-needle module is used to insert the sensor under a skin;

a triggering module, wherein when the triggering module moves towards a far end relative to the housing, the coupling of each of the at least two first buckles and corresponding one of the second buckles is released, in order to implement an installation action;

an elastic module, used to provide an elastic force required to implement the installation action, wherein the at least two first buckles are bendable and adapted to be bent to an outside of the housing, and when being bent, the coupling of the each of the at least two first buckles and the corresponding one of the second buckles is released.

2. The installation unit of the analyte detection device of claim 1, wherein the triggering module comprises fixed buckles corresponding to the at least two first buckles, and each of the fixed buckles are in contact with corresponding one of the at least two first buckles in the initial pre-installation configuration to prevent the at least two first buckles from bending to the outside of the housing.

3. The installation unit of the analyte detection device of claim 2, wherein when the triggering module moves toward the far end relative to the housing, the each of the fixed buckles do not contact the corresponding one of the at least two first buckles.

4. The installation unit of the analyte detection device of claim 2, wherein the at least two first buckles, the second buckles and the fixed buckles are located on a same horizontal plane.

5. The installation unit of the analyte detection device of claim 2, wherein a contact between the each of the fixed buckles and the corresponding one of the at least two first buckles is one of point-contact, line-contact and surface-contact.

6. The installation unit of the analyte detection device of claim 5, wherein the contact between the each of the fixed buckles and the corresponding one of the at least two first buckles is surface-contact, a contact surface is at a fixed angle with a horizontal plane, and converge at a near end.

7. The installation unit of the analyte detection device of claim 1, wherein a coupling place of the each of the at least two first buckles and the corresponding one of second buckles is a plane, the plane is at a fixed angle with a horizontal plane and converge at a near end.

8. The installation unit of the analyte detection device of claim 1, wherein the at least two first buckles are distributed on the housing at a same angle interval.

9. The installation unit of the analyte detection device of claim 1, wherein when the installation action is implemented, the elastic module pushes the parallel slider module and the auxiliary-needle module to move from an initial position toward a near end.

10. The installation unit of the analyte detection device of claim 9, wherein after the auxiliary-needle module moves towards the near end to a predetermined position, the parallel slider module and the auxiliary-needle module are disconnected, and the elastic module pushes the auxiliary-needle module back to the initial position.

11. A method of use of an installation unit of an analyte detection device, comprising:

providing an installation unit of analyte detection device which comprises a housing comprising at least two first buckles;

a parallel slider module provided with second buckles corresponding to the at least two first buckles, and the at least two first buckles and the second buckles are releasably coupled at a coupling in an initial pre-installation configuration;

an analyte detection device arranged at a front end of the parallel slider module, wherein the analyte detection device comprises a shell, a transmitter, a sensor and an internal circuit arranged in the shell and electrically coupled with the sensor;

an auxiliary-needle module, wherein the auxiliary-needle module and the parallel slider module are releasably connected to each other for inserting the sensor under a skin;

a triggering module, wherein when the triggering module moves to a far end relative to the housing, the coupling of each of the at least two first buckles and corresponding one of the second buckles is released to implement an installation action; and an elastic module providing an elastic force required to perform the installation action;

attaching an near end of the installation unit of the analyte detection device to the skin;

pressing the housing at the far end, wherein the triggering module moves to the far end relative to the housing to release the coupling of each of the at least two first buckles and the corresponding one of the second buckles;

pushing the parallel slider module and the auxiliary-needle module move from an initial position toward the near end by the elastic module, wherein the analyte detection device is installed on the skin while the sensor penetrates the skin;

wherein the parallel slider module is disconnected from the auxiliary-needle module, and the elastic module pushes the auxiliary-needle module back to the initial position; and removing remaining parts of the installation unit, wherein the at least two first buckles are bendable and adapted to be bent to an outside of the housing, and when being bent, the coupling of the each of the at least two first buckles and the corresponding one of the second buckles is released.

12. The method of use of the installation unit of the analyte detection device of claim 11, wherein the triggering module comprises fixed buckles corresponding to the at least two first buckles, and each of the fixed buckles are in contact with corresponding one of the at least two first buckles in the initial pre-installation configuration to prevent the at least two first buckles from bending to the outside of the housing.

13. The method of use of the installation unit of the analyte detection device of claim 12, wherein when the triggering module moves toward the far end relative to the housing, the each of the fixed buckles do not contact the corresponding one of the at least two first buckles.

14. The method of use of the installation unit of the analyte detection device of claim 12, wherein the at least two first buckles, the second buckles and the fixed buckles are located on a same horizontal plane.

15. The method of use of the installation unit of the analyte detection device of claim 12, wherein a contact between the each of the fixed buckles and the corresponding one of the at least two first buckles is one of point-contact, line-contact and surface-contact.

16. The method of use of the installation unit of the analyte detection device of claim 15, wherein the contact between the each of the fixed buckles and the corresponding one of the at least two first buckles is surface-contact, a contact surface is at a fixed angle with a horizontal plane, and converge at a near end.

17. The method of use of the installation unit of the analyte detection device of claim 11, wherein a coupling place of the each of the at least two first buckles and the corresponding one of second buckles is a plane, the plane is at a fixed angle with a horizontal plane and converge at a near end.

18. The method of use of the installation unit of the analyte detection device of claim 11, wherein the at least two first buckles are distributed on the housing at a same angle interval.

* * * * *